United States Patent [19]

D'Amico

[11] 4,427,436
[45] Jan. 24, 1984

[54] N-SUBSTITUTED XANTHATE BENZOTHIAZOLINE AND RELATED DERIVATIVES

[75] Inventor: John J. D'Amico, Creve Coeur, Mo.
[73] Assignee: Monsanto Company, St. Louis, Mo.
[21] Appl. No.: 397,617
[22] Filed: Jul. 12, 1982
[51] Int. Cl.³ ............... C07D 277/68; C07D 263/58; A01N 9/12
[52] U.S. Cl. .......................... 71/88; 71/90; 548/170; 548/221
[58] Field of Search ............ 548/170, 221; 71/90, 71/88

[56] References Cited

U.S. PATENT DOCUMENTS 4,171,213  10/1979  D'Amico .................. 71/90

FOREIGN PATENT DOCUMENTS 520363  11/1976  U.S.S.R. .................. 548/170

*Primary Examiner*—Robert Gerstl
*Attorney, Agent, or Firm*—Richard H. Shear; Raymond C. Loyer; J. Timothy Keane

[57] ABSTRACT

The present invention relates to compounds represented by the formula

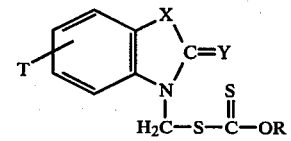

wherein R represents an alkyl radical having from 1 to 3 carbon atoms, and X and Y represent oxygen or sulfur, and T represents a radical selected from hydrogen and $C_{1-3}$ alkoxy. Those compounds have been found useful in a method for regulating plant growth and in plant growth regulant compositions.

36 Claims, No Drawings

N-SUBSTITUTED XANTHATE BENZOTHIAZOLINE AND RELATED DERIVATIVES

BACKGROUND OF THE INVENTION

This invention relates to certain N-substituted xanthate benzothiazoline and related derivatives which are useful in a method of regulating plant growth, especially leguminous plants.

Compounds which are useful in regulating the growth and development of crop plants have become of increasing interest in recent years. The use of non-nutrient chemicals which affect the growth pattern of crop plants is seen as an economical means to achieve desirable change in plants grown on a commercial scale. Such changes desirably improve the economic basis upon which the crops are grown and harvested.

As a result, there is a continuing effort to discover compounds useful as plant growth regulants which when utilized in a method of plant growth regulation provide an economic advantage far in excess of the cost of the compound and its application.

SUMMARY OF THE INVENTION

This invention is the discovery that compounds represented by the formula:

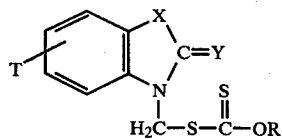

wherein R represents an alkyl radical having from 1 to 3 carbon atoms, T represents a radical selected from hydrogen and alkoxy, and X and Y are independently selected from oxygen and sulfur are plant growth regulants, especially leguminous plants. The compounds or compositions containing said compounds are applied to crop plants or to the locus of their growth in a method to achieve plant growth regulation.

DETAILED DESCRIPTION OF THE INVENTION

Compounds of the formula described above have been found to produce a variety of plant growth regulatory responses when applied to crop plants, especially leguminous crop plants, as for example, soybean (Glycine max). The terms "plant growth regulant effect", "plant growth regulation" or words to that effect are used in this specification and in the claims to mean the causation by the chemicals of the present invention, of a variety of plant responses which achieve a desirable promotion, inhibition or modification of any plant physiological or morphological process. It should additionally be recognized that various plant response may also result from a combination or sequence of both physiological and morphological factors.

The compound of this invention are prepared by the following reaction:

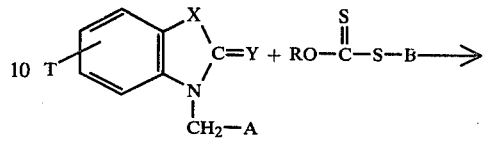

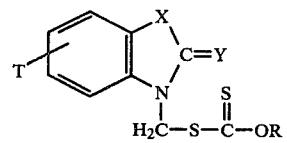

wherein R, T, and Y have the above described meanings. A represents a halogen and B represents an alkali metal.

The reaction is carried out in a suitable vessel utilizing a reaction medium which dissolves the reactants. Typically, the reaction medium is an organic solvent such as a $C_{1-3}$ alkyl alcohol or a ketone such as acetone. The reaction mixture is desirably agitated during the reaction and the reaction temperature elevated to slightly more than room temperature such as from about 25° to about 30° C. The reaction time under such conditioning is usually in the range of up to several days although varying reaction conditions such as temperature and pressure may alter the reaction rate.

Where the term "halogen" is employed herein, it is intended to mean chlorine, preferably bromine, iodine and fluorine. The term "alkali metal" is intended to mean sodium preferably potassium, lithium, rhubidium and cesium.

The term "active ingredient" is employed herein with reference to compositions containing at least one of the above described N-substituted xanthate benzothiazoline and related derivatives described above in combination with other ingredients. The compounds of this invention may be prepared according to the general procedure described in Example I below.

EXAMPLE 1

To a stirred slurry containing 0.11 mole of potassium ethyl or isopropyl xanthate in 200 ml of acetone, ethanol or isopropanol, 0.1 mol of 3-(chloromethyl)-2-benzothiazolinone, 3-(chloromethyl)-2-benzothiazolethione, 3-(chloromethyl)-2-benzoxazolethione, or 6-ethoxy-3-(chloromethyl)-2-benzothiazolethione was added in one portion. The reaction mixture was stirred at 25°-30° C. for three days. For all products 800 g of ice water was added and stirring continued at 0°-10° C. for 30 minutes. The solid was collected by filtration, washed with water until neutral to litmus and air-dried at 25°-30° C. The data are summarized in Table I.

TABLE I

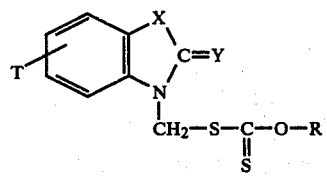

| Ex. No. | T | X | Y | R | Solvent | Mp. °C. | % Yield | % C Calcd. | % C Found | % H Calcd. | % H Found | % N Calcd. | % N Found | % S Calcd. | % S Found |
|---|---|---|---|---|---|---|---|---|---|---|---|---|---|---|---|
| 1 | H | S | O | —$C_2H_5$ | ethanol | 75–6[a] | 98 | 46.29 | 46.18 | 3.88 | 3.92 | 4.91 | 4.89 | 33.70 | 33.63 |
| 2 | H | S | O | —$CH(CH_3)_2$ | acetone | 83–4[a] | 83 | 48.13 | 48.10 | 4.38 | 4.41 | 4.68 | 4.70 | 32.12 | 32.02 |
| 3 | H | S | S | —$C_2H_5$ | ethanol | 86–7[b] | 93 | 43.83 | 43.80 | 3.68 | 3.67 | 4.65 | 4.67 | 42.54 | 42.46 |
| 4 | H | S | S | —$CH(CH_3)_2$ | isopropanol | 64–5 | 94 | 45.68 | 45.69 | 4.15 | 4.15 | 4.44 | 4.53 | 40.65 | 40.53 |
| 5 | H | O | S | —$C_2H_5$ | ethanol | 85–7 | 95 | 46.29 | 46.55 | 3.88 | 3.88 | 4.91 | 4.99 | 33.70 | 33.51 |
| 6 | 6-$OC_2H_5$ | S | S | —$C_2H_5$ | ethanol | 117–9[c] | 98 | 45.19 | 45.24 | 4.38 | 4.38 | 4.05 | 4.04 | 37.12 | 37.02 |

[a] Recrystallation from heptane - isopropanol
[b] Recrystallation from heptane - ethyl acetate
[c] Recrystallation from ethyl acetate The plant growth regulant effects which may be produced in crop plants, especially leguminous crop plants, using the method of the present invention are probably most readily observable as changes in the size, shape, color or texture of the treated plant or any of its parts. Similarly, changes in the quantity of the plant fruit or flowers are also quite apparent from visual inspection. The above changes may be characterized as an acceleration or retardation of plant growth, stature reduction, leaf or canopy alteration, increased branching, tillering, terminal inhibition, increased flowering or fruit set, increased root growth, axillary bud development or inhibition, delayed budding, increased cold hardiness, delayed or accelarated ripening, and the like.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Reduction in the maturation rate on portions of a crop permits an extended harvest period at peak yield and more efficient use of subsequent crop processing equipment. Suppression of vegetative growth at the appropriate stage of the plant's development may result in increased energy available for utilization in reproductive development so that, for example, more fruit or larger fruit is formed.

Increased plant dry matter accumulation is a valuable plant growth regulant response which can occur in conjunction with morphological changes or can be the sole plant growth response detected. Increased dry matter accumulation is the physically measurable manifestation of increase plant photosynthetic activity. Most plants capture no more than 1 to 3 percent of the solar energy they receive. Present knowledge suggest that it is theoretically possible to increase this rate to approximately twelve percent. Enhancement of photosynthesis at the appropriate stage of the plant's growth and development may enable the plant to fix more carbon dioxide resulting in the production of increased amounts of carbohydrate, amino acids, etc., which could be available for utilization in the plant's reproductive activities, leading to increased crop yields.

It is to be understood that the regulation of desirable crop plants in accordance with the instant invention does not include the total inhibition or the killing of such plants. It is contemplated herein to employ only plant regulating amounts of the compounds described in order to modify the normal sequential development of the treated plant to agricultural maturity. The application of a plant regulating amount may be applied to plants in sequence at various stages of the plant's development to obtain various desirable responses. As may be expected, and as is apparent to those skilled in the art, such plant regulating amounts will vary, not only with the material selected, but also with the modifying effect desired, the speciies of plant and its stage of development, the plant growth medium and whether a permanent or transitory effect is sought.

In accordance with this invention it has been found that desirable modification of crop plants, preferably leguminous crop plants, is achieved by applying the above-described plant growth regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. Should the application of the plant growth composition to the plant growth medium be desired, this is accomplished by incorporating the compositions in the soil or other media in the area where modifications of the plants is desired.

Compositions of this invention generally contain from about 5 to 95 parts active ingredient, about 1 to 50 parts surface-active agent, dispersant or the like, and about 5 to 94 parts solvent or carrier, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulating of plant growth, the active ingredients are applied in amounts of from 0.50 to about 5 pounds per acre. Preferred are foliar applications of from 0.50 to 5 pounds of the active ingredient per acre. In application to the soil habitat of germinant seeds, emerging seedlings and established vegetation for the regulation of plant growth, the active ingredients are applied in amounts of from 0.1 to about 5 pounds per acre or more. The application to the soil of from 0.1 to about 3 pounds of active ingredient per acre is preferred. Foliar application to plants beginning to blossom are preferred over other types of applications.

In accordance with the practice of the invention, several plant growth regulating compositions were formulated by mixing various N-substituted xanthate-3-benzothiazoline and related compounds as the active ingredient with acetone containing a surfactant and tested in accordance with the procedure described in Example 2.

EXAMPLE 2

A number of soybean plants, variety Williams, were grown from seeds in plastic pots in the greenhouse for a period of one week at which time the plants were thinned leaf (three weeks) was fully expanded, the plants were treated with a solution of the active ingredient in acetone and water. Aqueous TWEEN 20 was used as a surfactant.

When the fifth trifoliate leaf (four to five weeks) was fully expanded, the treated plants were compared with the non-treated control plants and the observations recorded.

Table II below summarizes the results and observations made in accordance with the above procedure.

TABLE II

| Compound of Example No. | Lbs Acre | Kilos Hectare | % Dry* Weight | Response |
|---|---|---|---|---|
| 1 | 0.1 | 0.112 | 85 | No response |
|   | 0.5 | 0.56 | 103 | No response |
|   | 2.5 | 2.8 | 76 | Leaf alteration new growth |
| 2 | 0.1 | 0.112 | 95 | No response |
|   | 0.5 | 0.56 | 110 | Leaf alteration new growth |
|   | 2.5 | 2.8 | 103 | Leaf alteration new growth |
| 3 | 0.1 | 0.112 | 71 | Leaf distortion; leaf distortion new growth; leaf alteration new growth; altered canopy, stature reduction. |
|   | .5 | 0.56 | 78 | Leaf distortion; leaf distortion new growth; leaf alteration new growth; altered canopy; stature reduction. |
|   | 2.5 | 2.8 | 62 | Leaf distortion; leaf distortion new growth; leaf alteration new growth; altered canopy; stature reduction. |
| 6 | 0.1 | 0.112 | 83 | Leaf alteration new growth |
|   | 0.5 | 0.56 | 78 | Leaf alteration new growth |
|   | 2.5 | 2.8 | 82 | Leaf distortion new growth |
| 6 | 0.1 | 0.112 | 77 | no response |
|   | 0.5 | 0.56 | 70 | leaf alteration |
|   | 2.5 | 0.28 | 73 | leaf alteration |
| 6 | 0.1 | 0.112 | 121 | no response |
|   | 0.5 | 0.56 | 100 | no response |
|   | 2.5 | 0.28 | 74 | Leaf alteration, leaf alteration new growth |

*Calculated as percent of control

Although this invention has been described with respect to specific modifications, the details thereof are not to be construed as limitations, for it will be apparent that various equivalents, changes and modifications may be resorted to without departing from the spirit and scope thereof and it is understood that such equivalents embodiments are intended to be included herein.

What is claimed:

1. A compound represented by the formula

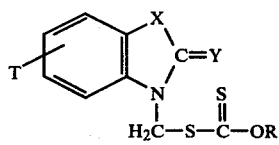

wherein R represents an alkyl radical having from 1 to 3 carbon atoms, X and Y are independently selected from oxygen and sulfur and T is a radical selected from hydrogen and $C_{1-4}$ alkoxy.

2. A compound of claim 1 wherein X and Y are sulfur.
3. A compound of claim 2 wherein T is hydrogen.
4. A compound of claim 1 wherein X is oxygen and Y is sulfur.
5. A compound of claim 1 wherein X is sulfur and Y is oxygen.
6. A compound of claim 1 wherein X and Y are oxygen.
7. A compound of claim 1 wherein R is ethyl.
8. A compound of claim 1 wherein R is ethyl and T is alkoxy.
9. A compound of claim 2 wherein R is ethyl and T is alkoxy.
10. A compound of claim 4 wherein R is ethyl and T is hydrogen.
11. A compound of claim 2 wherein R is selected from 2-propyl and ethyl and T is hydrogen.
12. A compound of claim 5 wherein R is selected from 2-propyl and ethyl and T is hydrogen.
13. A method of regulating the natural growth and development of crop plants which comprises apply to the plant locus a plant growth regulating non-lethal amount of a compound represented by the formula

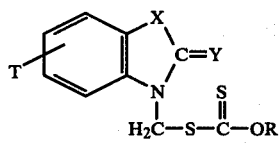

wherein R represents an alkyl radical having from 1 to 3 carbon atoms; X and Y are independently selected from oxygen and sulfur and T is a radical selected from hydrogen and $C_{1-4}$ alkoxy.

14. A compound of claim 1 wherein X and Y are sulfur.
15. A compound of claim 2 wherein T is hydrogen.
16. A compound of claim 1 wherein X is oxygen and Y is sulfur.
17. A compound of claim 1 wherein X is sulfur and Y is oxygen.
18. A compound of claim 1 wherein X and Y are oxygen.
19. A compound of claim 1 wherein R is ethyl.
20. A compound of claim 1 wherein R is ethyl and T is alkoxy.
21. A compound of claim 2 wherein R is ethyl and T is alkoxy.
22. A compound of claim 4 wherein R is ethyl and T is hydrogen.
23. A compound of claim 2 wherein R is selected from 2-propyl and ethyl and T is hydrogen.
24. A compound of claim 5 wherein R is selected from 2-propyl and ethyl and T is hydrogen.
25. A plant growth regulating composition comprising an adjuvant and an effective plant growth regulating amount of an active ingredient represented by the formula

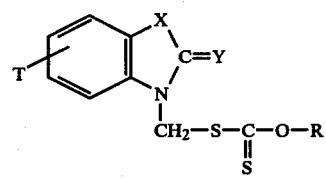

wherein R represents an alkyl radical having from 1 to 3 carbon atoms; X and Y are independently selected from oxygen and sulfur and T is a radical selected from hydrogen and $C_{1-4}$ alkoxy.

26. A compound of claim 1 wherein X and Y are sulfur.
27. A compound of claim 2 wherein T is hydrogen.
28. A compound of claim 1 wherein X is oxygen and Y is sulfur.
29. A compound of claim 1 wherein X is sulfur and Y is oxygen.
30. A compound of claim 1 wherein X and Y are oxygen.
31. A compound of claim 1 wherein R is ethyl.
32. A compound of claim 1 wherein R is ethyl and T is alkoxy.
33. A compound of claim 2 wherein R is ethyl and T is alkoxy.
34. A compound of claim 4 wherein R is ethyl and T is hydrogen.
35. A compound of claim 2 wherein R is selected from 2-propyl and ethyl and T is hydrogen.
36. A compound of claim 5 wherein R is selected from 2-propyl and ethyl and T is hydrogen.

* * * * *